United States Patent [19]
Munk

[11] Patent Number: 4,801,544
[45] Date of Patent: Jan. 31, 1989

[54] METHOD OF IMPROVING THE STORAGE LIFE OF LIQUID COMPOSITIONS CONTAINING ENZYMES

[75] Inventor: Barbara H. Munk, Albany, Calif.

[73] Assignee: The Clorox Company, Oakland, Calif.

[21] Appl. No.: 939,264

[22] Filed: Dec. 8, 1986

Related U.S. Application Data

[63] Continuation of Ser. No. 650,617, Sep. 12, 1984, abandoned.

[51] Int. Cl.⁴ ........................ C12N 9/96; C11D 10/02
[52] U.S. Cl. ............................... 435/188; 252/174.12; 252/162; 252/DIG. 12; 252/DIG. 14
[58] Field of Search ...................... 252/90, 92, 174.12, 252/170, DIG. 12, DIG. 14; 435/188

[56] References Cited

U.S. PATENT DOCUMENTS

| | | |
|---|---|---|
| 3,634,266 | 1/1972 | Theile et al. . |
| 3,687,853 | 8/1972 | Natali et al. . |
| 3,697,451 | 10/1972 | Mausner et al. . |
| 3,717,550 | 2/1973 | Ziffe . |
| 3,723,327 | 3/1973 | van Kampen et al. . |
| 3,741,902 | 6/1973 | Barrett, Jr. . |
| 3,746,649 | 7/1973 | Barrett, Jr. . |
| 3,775,331 | 11/1973 | Borrello . |
| 3,776,693 | 12/1973 | Smith et al. ........................ 252/170 |
| 3,840,480 | 10/1974 | Barrat et al. . |
| 3,953,353 | 4/1976 | Barrett, Jr. et al. . |
| 4,009,076 | 2/1977 | Green et al. . |
| 4,016,040 | 4/1977 | Win et al. . |
| 4,090,973 | 5/1978 | Maguire, Jr. et al. . |
| 4,142,999 | 3/1979 | Bloching et al. . |
| 4,169,817 | 10/1979 | Weber . |
| 4,243,546 | 1/1981 | Shaer . |
| 4,302,364 | 11/1981 | Gosset et al. . |
| 4,305,837 | 12/1981 | Kaminsky et al. . |
| 4,404,115 | 9/1983 | Tai . |
| 4,405,483 | 9/1983 | Kuzel et al. . |

FOREIGN PATENT DOCUMENTS 2042580 9/1980 United Kingdom .

OTHER PUBLICATIONS

Journal of Colloid and Interface Science, vol. 82, No. 1, Jul. 1981, "On the Phase Inversion in $H_2O$-Oil-Nonionic Surfactant Systems and Related Phenomena''-Hermann, et al.

Journal of Colloid and Interface Science, vol. 90, No. 1, Nov. 1982, "The Phase Behavior of Systems of the Type $H_2O$-Oil-Nonionic Surfactant-Electrolyte", M. Kahlweit.

*Primary Examiner*—Prince E. Willis
*Assistant Examiner*—John F. McNally
*Attorney, Agent, or Firm*—John A. Bucher

[57] ABSTRACT

Compositions effective in removing protein, fat and/or starch based stains as well as oil and grease based stains from fabrics comprise organic solvents admixed with surfactants and an enzyme component wherein the enzymes are dissolved in aqueous solution and the aqueous solution is, in turn, dispersed as reversed micelles within the solvent/surfactant mixture. Encapsulating the enzymes in reversed micelles protects them from degradation by the solvents and thereby prolongs the effectiveness of the enzymes for extended periods of time. The total water content of the compositions is kept below 5 weight % so that the compositions' oil and grease stain removal ability remains unimpaired.

3 Claims, No Drawings

METHOD OF IMPROVING THE STORAGE LIFE OF LIQUID COMPOSITIONS CONTAINING ENZYMES

This is a continuation of co-pending application Ser. No. 06/650,617 filed on Sept. 12, 1984, now abandoned.

BACKGROUND OF THE INVENTION

Modern home laundry cleaning compositions are very reliable and efficient in removing soil from household clothing articles, linens, and the like. Household laundry detergent compositions are formulated to remove soil and stains from various kinds of dirt depositions in the fabric. Generally such formulations effectively remove dirt induced soil and are even effective in removing low level stains or soil from oil or grease sources. However, common laundry detergents are deficient in handling soil resulting from protein sources, e.g., blood, grass; or soil where the proteins are combined with oils or greases from animal or vegetable origin; or soils of heavy grease, fats, or starch origin.

In order to effectively remove these difficult soils, various compositions are being marketed as "pre-washes" or "pre-spotters." Such compositions are applied directly to the difficult stains before the washing process. The "pre-wash" compositions are formulated primarily to remove oily or greasy stains. For this purpose, such compositions rely principally upon organic based solvents such as hydrocarbons, halogenated hydrocarbons etc. in combination with hydrocarbon compatible surfactants. Such compositions effectively dissolve and/or emulsify oily or greasy stains. These compositions, however, are not nearly as effective in removing stains caused by protein sources such as blood, and grass; or from combined protein and fat sources such as sebum; or from fats and starches. These sources produce stains which are difficult to remove with solvent/surfactant combinations alone.

In an effort to treat protein, fat and starch based stains, some producers have resorted to the use of enzyme compositions that are available from various sources. These compositions employ protease, amylase, or lipase enzymes to attack protein, fat and starch based stains and chemically degrade these compounds so that they can more readily be removed by subsequent or concurrent treatment with conventional surfactants. While enzyme containing compositions are quite proficient in treating such stains, the enzymes themselves are quite susceptible to deactivation if mixed with other components, especially hydrocarbon solvents.

Thus the "pre-wash" manufacturer faces a dilemma if it is desired to effectively treat both oil and grease based stains as well as protein, fat and/or starch based stains on the same garments. Since enzymes are incompatible with hydrocarbon solvents, it has heretofore been impractical to devise a single enzyme-hydrocarbon solvent product that will effectively treat both grease stains and protein, fat and/or starch stains. It is not practical to provide two separate formulations, one enzyme and one solvent, since separate compositions would be more costly; and cause twice the work for the user. Therefore such separate treatment procedures are unacceptable to the consumer.

The ideal solution to the problem would be a "pre-wash" composition which would simply and easily treat both grease and protein, fat, and/or starch stains in a single treatment. Such a composition should have a reasonable storage life during which the enzymes would not excessively degrade or deteriorate; it should be quite liquid so that it could be easily applied to the stains, as by spraying; it should be a single phase composition, so that one component would not settle out thereby requiring agitation or shaking to mix the components before use; and it should be dispersible in, or miscible with laundry wash water so that it is easily removed when the fabrics are subsequently washed in a conventional washing machine.

The present invention solves the problems enumerated above.

BRIEF DESCRIPTION OF THE INVENTION

The present invention relates to laundry "pre-wash" compositions; and more particularly to pre-wash compositions that are single phase liquids effective against both oil and grease stains as well as protein, fat and/or starch stains. The invention compositions effectively combine the advantages of both hydrocarbon oil and grease solvents and enzymes in a single liquid composition. The normally incompatible hydrocarbon solvents and enzymes are combined without excessly limiting the products' "shelf-life", i.e., the enzyme component retains an effective activity against stains for extended periods; and the hydrocarbon solvents retain their effectiveness against oil and grease stains.

The enzymes are water soluble and they must remain in aqueous solution to retain their activity against proteins, fats, and/or starches. The hydrocarbon solvents, on the other hand are quite hydrophobic and immiscible in aqueous solutions. The hydrocarbon solvents are effective against oil and grease in the absence of water. Any water present in the "pre-wash" composition tends to interfere with the solvents' ability to remove oil and grease.

The present compositions reconcile these adverse properties by dispensing aqueous solutions of the enzymes as "reversed micelles" within the hydrocarbon solvent/sufactant medium. The "reversed micelles" are formed by providing suitable surfactants which facilitate encapsulation of an aqueous solution of the enzymes and subsequently dispersing the enzyme/surfactant mixture in the hydrocarbon solvent medium. The enzymes are dissolved in the aqueous solution; surfactants are added. The surfactants encapsulate the enzymes, and then permit the dispersion of the enzyme-aqueous portion in the hydrocarbon medium.

In other words, the surfactants effectively facilitate the formation of reversed micelles. In such reversed micelles the hydrophobic tail of the surfactant dissolves in the hydrocarbon medium, while the hydrophilic head of the surfactant dissolves in the aqueous enzyme solution. Under appropriate conditions minute micelles are formed within the hydrocarbon medium. The enzymes are dissolved within the aqueous micelle interior where they are effectively protected from attack and degradation by the hydrocarbon solvent.

When the "pre-wash" composition is applied to a fabric, the hydrocarbon component attacks and removes the oil and grease stains without interference from the aqueous portion of the composition since the aqueous portion is but a minor amount, 5% or less, of the composition. At the same time, the enzymes are released upon the fabric surface where they can effectively attack the protein, fat, and/or starch stains.

The aqueous enzyme-surfactant "reversed-micelles" are extremely small and are dissolved within the hydrocarbon medium to form a suspension or dispersion. Thus there is no problem with phase separation. Further, due to the unique fine structure, i.e., reversed micelles, the enzymes in the aqueous portion are protected from premature degradation by the surrounding hydrocarbon medium.

From a component standpoint the invention compositions comprise a small percentage (by weight) of the enzymes; somewhat larger percentages of enzyme stabilizers, e.g., sodium chloride, calcium chloride, or triethanolamine, all of which are dissolved in aqueous solution with the total water content being less then 5% of the composition; substantial percentages of one or more surfactants, preferably nonionic; and a large percentage of hydrocarbon solvent. In addition, small percentages of hydrotropes, such as glycols may also be present. Small amounts of perfumes or dyes may be included for aesthetic purposes.

The pre-wash compositions are prepared in a prescribed procedure so as to produce a solution of reversed micelles having the aqueous enzyme solution held within the interior thereof; and with the micelles dispersed throughout the hydrocarbon solvent-surfactant medium.

In general, the compositions may comprise several tenths of a percent of solution (as a glycol/water solution) enzyme; about a tenth of a percent of NaCL (as enzyme stabilizer); less than five percent water; about twenty-five to thirty-five percent surfactant; about sixty to seventy percent hydrocarbon solvent; about two to three percent of a glycol as a hydrotrope; and if desired, several tenths of percent perfume and coloring material (dye).

In a preferred composition the water dissolved enzyme may comprise about 0.2 weight%; about 1.5 weight% of 1M NaCl aqueous solution; about 2.5 weight% of ethylene glycol; about 14.5 weight% of an ethoxy-propyloxy linear alcohol nonionic surfactant; about 14.5 weight% of an ethoxylated linear alcohol nonionic surfactant; with the remainder being hydrocarbon solvent, e.g., a nominal C-12 to C-16 mixture of isoparaffins. Very small percentages of perfumes or coloring agents may be added.

It will be understood that the enzyme component is present to effectively remove protein based stains, fat based stains, and/or starch based stains. Of these types of stains the most important are the protein based stains resulting from blood, grass, body fluids, and the like. Therefore, proteases are most desirable in the invention compositions. It should also be apparent that related enzymes having particular effectiveness against other organic molecules, e.g., starches, fats, etc., may also be included along with the proteases. If desired, amylases, lipases etc. may be combined with the protease enzymes to produce a pre-wash composition that is effective against a full spectrum of fabric stains. The only precaution to be taken if additional enzymes are introduced, is that such added enzymes be compatible with the protease.

It is most important that the total amount of water in the compositions be maintained at levels no greater than 5 weight%. Quantities of water greater than 5 weight% may interfere with the ability of the hydrocarbon solvent to effectively remove oil and grease stains.

It is an object of the invention to provide improved pre-wash compositions.

It is another object of the invention to provide compositions that are useful for removing both oil and/or grease based stains and protein, fat, and/or starch based stains from fabrics.

It is another object of the invention to provide compositions wherein enzymes in aqueous solution are encapsulated in surfactants dispersed within a surfactant-hydrocarbon solvent medium to form reversed micelles therein.

It is still another object of the invention to provide compositions including hydrocarbon solvents, surfactants, and enzymes as active ingredients and wherein the enzymes are protected from the hydrocarbon solvent by encapsulating the enzymes within surfactants and then dispersed in the solvent to form reversed micelles.

It is yet another object of the invention to provide a method for encapsulating enzymes in aqueous solution within reversed micelles dispersed in a surfactant-hydrocarbon solvent medium.

Other objects and advantages of the invention will become apparent from the following specification and claims.

DETAILED DESCRIPTION OF THE INVENTION

Pre-wash compositions that exhibit the ability to simultaneously remove oil/grease stains and protein, fat, and/or starch stains from fabrics are formulated from surfactants, enzymes, and hydrocarbon solvents. While enzymes and hydrocarbon solvents are normally incompatible, the invention compositions overcome this difficulty by enclosing the enzymes in nonionic surfactants, and then dispersing the mixture in hydrocarbon solvents. Reversed micelles are thus formed in the surfactant-hydrocarbon medium. The water content of the compositions is kept very low, i.e., no more than 5 weight%, so that the oil and grease stain removing ability of the hydrocarbon solvent substrate remains unimpaired. At the same time the encapsulated enzymes are released to attack protein stains when the pre-wash composition is applied to soiled fabrics.

More specifically, the pre-wash compositions comprise a hydrocarbon solvent medium in which surfactants are dispersed, as well as an aqueous enzyme solution in the form of reversed micelles. The dispersed surfactants form the "micelle" interface between the aqueous enzyme solution and the surrounding hydrocarbon solvent medium. The hydrocarbon solvent comprises the major component, ideally being present in amounts greater than 60% by weight. The surfactants comprise the next most abundant component, ideally being present in an aggregate amount in the neighborhood of 30%. It is desirable that the solvent-surfactant ratio be maintained at about 2:1, e.g., if the solvent is about 60%, then the surfactants should be present at about 30%. The total amount of solvent and surfactant is not critical; however, together they should comprise well over 90% of the composition.

The component that is critical to the effectiveness of the pre-wash compositions is water. Water comprises the solvent for the enzymes and its presence is necessary for that purpose. However, it has been determined that if water is present in quantities greater than about 5% by weight, the oil and grease removal efficiency of the hydrocarbon solvent is adversely affected. When the water content rises appreciably above 5%, there is a noticeable decrease in the solvents' ability to thoroughly remove oil and grease stains. Therefore, the water content is always kept at 5% or less, preferably less.

The water acts as a solvent for the enzyme component, which is necessary to remove protein, fat and/or starch based stains. The enzymes are dissolved in the water. The enzymes are stabilized in the aqueous solution by the addition of salt (NaCl). Only a small percentage, e.g., several tenths of a percent of the enzyme solution is needed to be effective. Higher amounts of enzymes may also be utilized, but will add to the cost of materials. In commercially available enzyme solutions having an enzyme activity equivalent to 8 K.N.P.U. (K.N.P.U. means Kilo Novo Protease Units. There is no industry-wide standard for measuring activity.), about 0.2% by weight is an effective amount. Such enzyme solutions may be further stabilized by the addition of 1-2% of a 1M NaCl solution.

A hydrotrope, such as ethylene glycol can be added in low percentages, e.g., 2-3%, to aid the solubility of the surfactants in the solvent.

It will be understood that, except for the limit on water in the compositions, the percentages of all components may be varied over relatively wide ranges, i.e., there is nothing critical about the hydrocarbon solvent, surfactants, enzyme, salt or glycol percentages. On the other hand, experimentation has developed a preferred composition having the following percentages of components:

| Component | Wt % |
|---|---|
| Enzyme (Savinase 8.0L) (Enzyme dissolved in a solution of 80% propylene glycol/20% $H_2O$) | 0.2 |
| NaCl (1M in water) | 1.5 |
| Ethylene glycol | 2.5 |
| Nonionic surfactants (50-50 mixture of ethyoxylated linear alcohols and ethoxylated-propoxylated linear alcohols) | 29.5 |
| Hydrocarbon solvent (isoparaffins) having nominal 12 to 16 carbons) | 66.0 |
| Perfume and dye | remainder. |

When produced in accordance with the procedure set forth below, the compositions are a clear solution with the enzymes encapsulated in reversed micelles within the surfactant-hydrocarbon solvent medium. The compositions exhibit excellent activity against both oil and grease stains as well as protein, and/or starch and/or fat-based stains. The compositions also retain an appreciable portion of the enzyme activity when stored for extended periods.

The selection of the enzymes for use in the compositions may be made from any number of commercially available liquid enzyme solutions that are useful against proteins, lipids, and starchy substances. Such enzyme solutions are available from several commercial sources.

For instance, the commercially available alkaline proteases (preferred in the invention) are derived from various strains of the bacterial *Bacillus subtilis.* These proteases are also known as subtilisins, and are available under the trademarks Esperase®, Savinase®, and Alcalase®, from Novo Industri A/S, of Bagsvaerd, Denmark; and also under the trademarks Maxatase® and Maxacal® from Gist-Brocades N.V. of Delft, Netherlands.

These commercially available proteases are supplied as aqueous stabilized solutions of the enzyme. The enzymes are generally stabilized by the addition of glycols such as propylene glycol. These solutions are also supplied in various strengths wherein the strengths are defined by the activity exhibited by the enzyme. Thus as noted above, in the preferred composition the enzyme solution has an activity of 8 K.N.P.U. Of course, enzyme solutions of lesser or greater activity can be utilized in the invention compositions.

It should be noted that other enzymes may be used in the compositions in addition to, or in place of, the proteases. Thus lipases effective against fats; or amylases, effective against starches, can also be used in the formulations. Both types of enzymes are commercially available, e.g. lipases-(see U.S. Pat. No. 3,950,277 column 3, lines 15-55 for a description of lipase enzymes, their origins, and sources-incorporated herein by reference); amylases-Rapidase® from Société Rapidase, France; and Milezyme® from Miles Labs., Elkhurst, Ind.

It has been determined that the addition of salt, NaCl, to the enzyme solutions will further stabilize the enzymes against degradation in the presence of the hydrocarbon solvents of the pre-wash compositions. To this end, the compositions also include aqueous salt solution as stabilizing agent. While the exact amount of the stabilizer is not critical, the inclusion of roughly 1.5 weight% of 1M NaCl to the aqueous enzyme solution has been found to aid in maintaining enzyme activity when the product is stored.

Surfactants comprise a major component of the prewash compositions. Surfactants that are compatible with the hydrocarbon solvent medium are most necessary; and in addition such surfactants must not degrade, or interfere with the enzymes in the reversed micelles. The surfactants are also responsible for the micelle formation within the hydrocarbon medium. Nonionic surfactants are ideal for the above stated purposes. The long chain alcohols such as linear ethoxylated and linear propoxylated alcohols and mixtures thereof are particularly useful in the invention compositions. Such surfactants are completely compatible with the hydrocarbon solvents; they efficiently form reversed micelles to encapsulate the aqueous enzyme solutions; they do not degrade the enzymes; and they contribute significantly to the removal of soil from fabrics to which the compositions are applied.

Alkyl ethoxylated and propoxylated alcohols in the nominal C-12 to C-16 range are most preferred. Such surfactants are available as standard articles of commerce under the name "Biosoft" from the Stepan Chemical Co.; or under the name "Neodol" from the Shell Chemical Co. The "Biosoft" series of nonionic surfactants are ethoxylated and propoxylated fatty alcohols sold in liquid form. The "Neodol" series of surfactants comprise a large group of nonionic surfactants including ethoxylated long chain alcohols with ethoxy groups ranging from 3 to 12 and the carbon chains averaging from about 9 to 15 carbons.

All such nonionic surfactants are useful in the invention compositions, although Neodol 25-3 is preferred. Neodol 25-3 is composed of carbon chains nominally in the C-12 to C-15 range with an average of three ethoxy moieties per mole of alcohol. Biosoft EA-10 is a mixture of ethoxylated and propoxylated long chain fatty alcohols wherein the carbon chains are nominally in the C-10 to C-12 range with an average of 7.1 ethoxy and 2 propoxy moieties per mole of alcohol.

Other similar nonionic surfactants can be substituted for the aforementioned surfactants in the compositions so long as they met the criteria set forth above.

The surfactants are included in the compositions in substantial quantities making up somewhat less than one-third of the weight. While the total surfactant percentage is not critical, they should be present in roughly one-half the amount of hydrocarbon solvent. It has been found that this ratio of surfactant to solvent is necessary to achieve good removal of oil and grease based soil wherein both the hydrocarbon solvent and surfactants play key roles.

The hydrocarbon solvent is the major component in the compositions and, in conjunction with the surfactants, is the primary agent for treating oil and grease based stains. The hydrocarbon solvent comprises well over half the compositions by weight; generally the percentages are in the 60–70% range.

The solvent component can be selected from any number of hydrocarbon based oil and grease solvents. Such materials are staple industrial products and may be procured from a number of oil industry sources.

It is necessary however that the solvent component be compatible with the formation of micelles, in this instance reversed micelles, i.e., micelles having an encapsulated aqueous component dispersed within an organic solvent medium. Because of this requirement it is desirable to employ solvents that are low in sulfur, acids, and oxygenated compounds. Pure hydrocarbon solvents, especially paraffinic hydrocarbons having fairly long carbon chains, e.g., C-10 to C-14 are highly preferred for use in the compositions. Such solvents are available from the Exxon Corporation of Houston, Tex. under the trademark "Isopar" and "Norpar". Both of these groups of hydrocarbon solvents have a very high (~98%) normal or isoparaffin content and very low concentrations of sulfur, acids, carbonyls, chlorides, etc. These solvents, or their equivalents from other manufacturers, are the preferred organic solvents for use in the compositions.

In order to produce the compositions wherein the aqueous enzyme component is protected from degradation by the organic solvents, i.e., encapsulation within reversed micelles, it is necessary to proceed according to the following method:

The desired amount of aqueous salt solution is prepared. The aqueous/glycol enzyme solution as procured from the manufacturer is then mixed into the salt solution. (Gentle agitation is used throughout the production process to thoroughly mix all components. Violent agitation is to be avoided as it may actually degrade the enzymes by a physical shearing of the enzyme molecules.)

A portion, perhaps one half, of the surfactant is then gently mixed into the aqueous enzyme/salt solution. After thorough mixing is obtained, the remainder of the surfactant is then added and thoroughly mixed in. At this stage, the aqueous enzyme/salt/surfactant mixture is a rather viscous clear liquid. The glycol component is then added with continuous mixing; after which, the hydrocarbon solvent is gradually added to form the finished product.

The final product is a clear transparent liquid, principally solvent and surfactant with small amounts (~5%) of water, and smaller amounts of enzyme and enzyme stabilizer.

Although the preparation procedure seems very straightforward and uncomplicated, it is emphasized that the sequence of addition of components should be closely adhered to. It is particularly important to first mix the components that dissolve in the aqueous phase; secondly mix in the surfactants; and finally add the hydrophobic organic solvent component. Any variation in the procedure may fail to produce the desired reversed micelles and the enzymes will be unprotected from the solvent components. Failure to produce the protective micelles will be apparent if a cloudy solution is produced; or if a precipitate forms upon standing.

The clear liquid product may be packaged in any suitable container and stored for periods of several months and yet retain a good percentage of the enzyme activity. When used it is preferred to spray the product on the soiled fabrics a few minutes before placing them into a washing machine. Normal laundering procedures may be utilized. Of course, an effort should be made to spray the product directly on the visibly soiled portions of the fabric as direct contact will ensure full opportunity for attacking the oil/grease, and/or protein, fat or starch stains prior to the laundering process.

When prepared according to the above directions, the enzyme stability of the compositions as noted above is quite good. In one test over 50% of the enzymes' initial activity remained after six month's storage at 70° F.

In another group of tests loss in enzyme activity with time was studied for the following composition made in accordance with the preferred method of the invention:

| Component | Wt. % |
|---|---|
| Savinase 8.0L | 0.2 |
| 1M NaCl (aq.) | 1.5 |
| Ethylene glycol | 2.5 |
| Biosoft EA-10 | 14.65 |
| Neodol 25-3 | 14.65 |
| Isopar L | 66.3 |
| Perfume | 0.2 |

Samples of the above composition were then stored at various temperature for a period of six months. Table I below sets/forth the results of tests on enzyme activity at the end of the six month period.

TABLE I

| Enzyme Activity After Six Months Storage | | |
|---|---|---|
| Storage temperature | Wt. % active enzyme | % activity* remaining |
| 35° F. | 0.17 | 85 |
| 70° F. | 0.11 | 55 |
| 100° F. | 0.02 | 10 |

*assumes 0.2 wt. % active enzyme in original sample

A series of studies were carried out to evaluate the efficacy of the enzyme containing pre-wash compositions of the invention.

In a first series, a number of compositions were prepared wherein the enzyme content was varied from 0 up to 1.0%. These compositions were then tested for effectiveness against various types of stains, i.e., grass, ballpoint pen ink, dirty motor oil, and azocasein. Laundry detergent and a commercial pre-wash formulation (designated "control"), were, in each instance, used for comparison purposes. Table II below sets forth the compositions. Tables III, IV and VII set forth the results of % stain removal as measured by instrument. Tables V, VI, and VIII set forth the results measured by visual grading (on a scale of 1-5, with 5 highest, 1 lowest).

TABLE II

| Composition (Wt %) | Formula A | Formula B | Formula C |
|---|---|---|---|
| | Formula Composition | | |
| Savinase 8.0L | 0-1 | 0-1 | 0-1 |
| Salt Water (1M NaCl) | 5 | 5 | 5 |
| Biosoft EA-4 | 14-15 | 13.3-15 | 13-15 |
| Biosoft EA-10 | 14-15 | 13.3-15 | 13-15 |
| Petro 22* | 0 | 0 | 1 |
| Ethylene Glycol | 0 | 2.5 | 2.5 |
| Isopar L | 65.3-66.3 | 65-66.3 | 64.3-66.3 |
| Perfume | 0.2 | 0.2 | 0.2 |

*alkyl naphthalene sulfonate, Na salt (wetting agent).

[1]The control prewash is a commercial product with no enzymes and utilized in these tests for comparison purposes.

TABLE III

PERFORMANCE TESTING
STAIN REMOVAL AZOCASEIN[1]

| | FABRIC | | | | | |
|---|---|---|---|---|---|---|
| | COTTON | | | POLYESTER | | |
| Basic Formula | A | B | C | A | B | C |
| Wt. % Enzyme | | | | | | |
| 0 | 13.6 | 10.8 | 6.6 | 15.0 | 11.7 | 12.3 |
| 0.1 | 41.5 | 36.2 | 37.9 | 43.9 | 45.2 | 48.2 |
| 0.2 | 39.5 | 32.4 | 49.8 | 47.8 | 41.2 | 55.2 |
| 0.4 | 53.8 | 45.2 | 46.3 | 51.5 | 55.4 | 57.2 |
| 0.8 | 56.2 | 59.8 | 54.5 | 57.6 | 59.6 | 54.7 |
| 1.0 | 55.5 | 43.0 | 55.4 | 58.7 | 40.7 | 62.4 |
| Control | | 17.2 | | | 15.7 | |
| Detergent | | 10.3 | | | 6.7 | |
| LSD* | | 17.2 | | | 15.8 | |

*LEAST SIGNIFICANT DIFFERENCE

[1]"azocasein" is a model stain designed to measure enzyme activity.

TABLE IV

PERFORMANCE TESTING
% STAIN REMOVAL
GRASS

| | FABRIC | | | | | |
|---|---|---|---|---|---|---|
| | COTTON | | | POLYESTER | | |
| BASIC FORMULA | A | B | C | A | B | C |
| Wt. % Enzyme | | | | | | |
| 0 | 56.8 | 64.8 | 58.4 | 64.2 | 64.2 | 59.6 |
| 0.1 | 90.9 | 92.3 | 90.0 | 89.9 | 93.6 | 92.6 |
| 0.2 | 91.7 | 92.6 | 93.5 | 92.9 | 94.5 | 96.2 |
| 0.4 | 93.5 | 94.5 | 92.2 | 96.0 | 95.6 | 95.5 |
| 0.8 | 92.2 | 94.4 | 93.8 | 95.3 | 97.6 | 96.1 |
| 1.0 | 92.6 | 93.3 | 94.0 | 96.1 | 97.1 | 97.0 |
| Control | | 56.6 | | | 60.3 | |
| Detergent | | 42.2 | | | 62.7 | |
| LSD | | 4.5 | | | 5.8 | |

TABLE V

PERFORMANCE TESTING
VISUAL GRADING
GRASS

| | FABRIC | | | | | |
|---|---|---|---|---|---|---|
| | COTTON | | | POLYESTER | | |
| BASIC FORMULA | A | B | C | A | B | C |
| Wt. % Enzyme | | | | | | |
| 0 | 1.5 | 1.5 | 1.6 | 1.0 | 1.1 | 1.0 |
| 0.1 | 3.4 | 3.8 | 3.2 | 1.8 | 2.1 | 2.0 |
| 0.2 | 3.9 | 3.6 | 4.1 | 2.2 | 2.3 | 2.3 |
| 0.4 | 4.1 | 4.2 | 4.1 | 2.7 | 2.4 | 2.4 |
| 0.8 | 4.0 | 4.1 | 4.3 | 2.7 | 2.7 | 2.8 |
| 1.0 | 4.0 | 3.6 | 4.1 | 2.9 | 2.9 | 3.1 |
| Control | | 1.4 | | | 1.0 | |
| Detergent | | 1.3 | | | 1.0 | |

TABLE V-continued

PERFORMANCE TESTING
VISUAL GRADING
GRASS

| | FABRIC | | | | | |
|---|---|---|---|---|---|---|
| | COTTON | | | POLYESTER | | |
| BASIC FORMULA | A | B | C | A | B | C |
| LSD | | 0.2 | | | 0.2 | |

TABLE VI

PERFORMANCE TESTING
VISUAL GRADING
BALLPOINT INK

| | FABRIC | | | | | |
|---|---|---|---|---|---|---|
| | COTTON | | | POLYESTER | | |
| BASIC FORMULA | A | B | C | A | B | C |
| Wt. % Enzyme | | | | | | |
| 0 | 3.1 | 2.4 | 2.6 | 1.1 | 1.4 | 1.1 |
| 0.1 | 2.0 | 2.7 | 2.5 | 1.3 | 1.1 | 1.2 |
| 0.2 | 2.8 | 2.3 | 3.4 | 1.2 | 1.2 | 1.1 |
| 0.4 | 2.9 | 3.1 | 3.0 | 1.1 | 1.0 | 1.4 |
| 0.8 | 1.7 | 3.3 | 2.3 | 1.1 | 1.1 | 1.2 |
| 1.0 | 3.2 | 2.5 | 2.6 | 1.5 | 1.0 | 1.5 |
| Control | | 3.3 | | | 2.0 | |
| Detergent | | 1.0 | | | 1.1 | |
| LSD | | 0.4 | | | 0.1 | |

TABLE VII

PERFORMANCE TESTING
% STAIN REMOVAL
DIRTY MOTOR OIL

| | FABRIC | | | | | |
|---|---|---|---|---|---|---|
| | COTTON | | | POLYESTER | | |
| BASIC FORMULA | A | B | C | A | B | C |
| Wt. % Enzyme | | | | | | |
| 0 | 92.8 | 94.2 | 92.3 | 78.7 | 82.1 | 85.1 |
| 0.1 | 93.6 | 92.1 | 92.3 | 84.2 | 71.0 | 75.3 |
| 0.2 | 93.6 | 93.4 | 92.2 | 84.7 | 79.3 | 80.5 |
| 0.4 | 94.9 | 94.7 | 92.3 | 82.0 | 78.3 | 83.1 |
| 0.8 | 93.4 | 93.6 | 92.5 | 84.1 | 74.8 | 70.8 |
| 1.0 | 93.7 | 85.4 | 93.0 | 84.0 | 75.5 | 81.6 |
| Control | 94.5 | | | 85.4 | | |
| Detergent | | 47.1 | | | 6.3 | |
| LSD | | 3.8 | | | 9.2 | |

TABLE VIII

PERFORMANCE TESTING
VISUAL GRADING
DIRTY MOTOR OIL

| | FABRIC | | | | | |
|---|---|---|---|---|---|---|
| | COTTON | | | POLYESTER | | |
| BASIC FORMULA | A | B | C | A | B | C |
| Wt. % Enzyme | | | | | | |
| 0 | 3.9 | 3.7 | 3.6 | 2.7 | 1.8 | 3.0 |
| 0.1 | 3.6 | 3.7 | 3.9 | 2.7 | 2.1 | 2.2 |
| 0.2 | 3.5 | 3.5 | 3.8 | 2.3 | 2.0 | 2.2 |
| 0.4 | 3.8 | 3.8 | 3.6 | 2.8 | 2.5 | 2.5 |
| 0.8 | 3.4 | 3.5 | 3.2 | 2.7 | 2.4 | 1.6 |
| 1.0 | 3.8 | 3.9 | 3.3 | 2.5 | 2.2 | 2.3 |
| Control | 4.0 | | | 2.3 | | |
| Detergent | | 1.4 | | | 1.0 | |
| LSD | | 0.3 | | | 0.4 | |

A review of the data in Tables III, IV, V, VI, VII, and VIII above will make it apparent that as little as 0.1% added enzyme produces a significant increase in the ability of the compositions to remove azocasein and grass stains.

In a second series of tests, another group of invention compositions were prepared and tested along with the control, commercial pre-wash and laundry detergent against a broad range of stains. In this second series, the enzyme content was kept constant at 0.2%. Table IX sets forth the various compositions. Tables X, XI, and XII set forth the results when the formulations were tested against the indicated stains on 100% cotton fabric, 65/35 polyester/cotton fabric, and 100% polyester fabric.

TABLE IX

| | Formula Composition | | | |
|---|---|---|---|---|
| | Formula 1 wt % | Formula 2 wt % | Formula 3 wt % | Formula 4 wt % |
| Savinase 8.0L | 0.2 | 0.2 | 0.2 | 0.2 |
| Salt Water (1MNaCl) | 1.5 | 3.0 | 1.5 | 3.0 |
| Water | 0 | 0 | 0 | 0 |
| Ethylene Glycol | 2.5 | 2.5 | 0 | 0 |
| Petro 22 | 0 | 0 | 0 | 0 |
| Biosoft EA-4 | 14.65 | 13.9 | 15.0 | 15.0 |
| Biosoft EA-10 | 14.65 | 13.9 | 15.0 | 15.0 |
| Isopar L | 66.3 | 66.3 | 68.1 | 66.6 |
| Perfume | 0.2 | 0.2 | 0.2 | 0.2 |

TABLE X

| | PERFORMANCE EVALUATION 100% COTTON | | | | | | | | | | | | |
|---|---|---|---|---|---|---|---|---|---|---|---|---|---|
| | FORMULA 1 | | FORMULA 2 | | FORMULA 3 | | FORMULA 4 | | CONTROL | | DETERGENT | | |
| | HOT | WARM | HOT | WARM | HOT | WARM | HOT | WARM | HOT | WARM | HOT | WARM | LSD |
| INSTRUMENTAL GRADING STAINS: | | | | | | | | | | | | | |
| Chocolate Ice Cream | 91.2 | 91.3 | 91.2 | 92.0 | 92.1 | 92.6 | 91.2 | 91.9 | 90.9 | 92.0 | 90.6 | 90.5 | 1.1 |
| Azocasein | 36.1 | 33.8 | 42.0 | 31.9 | 41.1 | 37.8 | 39.9 | 34.1 | −0.5 | −1.0 | 4.9 | −3.0 | 4.8 |
| Egg | 99.2 | 99.2 | 98.9 | 98.7 | 99.1 | 98.8 | 99.1 | 98.8 | 98.8 | 98.6 | 98.3 | 98.7 | 0.4 |
| Grass | 95.2 | 93.2 | 95.7 | 93.5 | 95.4 | 95.6 | 95.0 | 93.1 | 67.9 | 65.4 | 56.9 | 59.0 | 2.3 |
| Spaghetti Sauce | 94.2 | 91.9 | 92.7 | 91.8 | 92.8 | 93.8 | 92.2 | 91.9 | 89.4 | 89.3 | 86.1 | 86.3 | 1.3 |
| Dirty Motor Oil | 94.8 | 94.6 | 94.6 | 92.5 | 93.9 | 94.4 | 93.4 | 93.9 | 93.4 | 93.2 | 42.7 | 41.6 | 2.3 |
| Blood | 98.2 | 98.5 | 98.2 | 98.4 | 98.0 | 98.0 | 97.8 | 97.8 | 94.6 | 97.0 | 97.0 | 96.8 | 0.6 |
| VISUAL GRADING STAINS: | | | | | | | | | | | | | |
| Grass | 4.5 | 4.1 | 4.4 | 4.3 | 4.4 | 4.4 | 4.2 | 4.3 | 2.4 | 2.4 | 1.8 | 2.1 | 0.2 |
| Spaghetti Sauce | 3.5 | 3.3 | 3.6 | 3.6 | 3.5 | 3.8 | 3.5 | 3.7 | 2.9 | 3.2 | 2.6 | 2.6 | 0.2 |
| Dirty Motor Oil | 4.2 | 4.4 | 4.4 | 4.2 | 4.3 | 4.4 | 4.3 | 4.2 | 4.2 | 3.9 | 1.1 | 1.2 | 0.2 |
| Blood | 4.1 | 4.3 | 4.3 | 4.2 | 4.3 | 4.1 | 4.0 | 4.1 | 2.8 | 3.7 | 3.8 | 3.8 | 0.2 |
| Ballpoint Ink | 3.0 | 2.4 | 3.2 | 2.9 | 2.6 | 2.2 | 2.2 | 2.5 | 2.9 | 3.7 | 1.5 | 1.4 | 0.2 |

TABLE XI

| | PERFORMANCE EVALUATION 65/35 POLYESTER/COTTON | | | | | | | | | | | | |
|---|---|---|---|---|---|---|---|---|---|---|---|---|---|
| | FORMULA 1 | | FORMULA 2 | | FORMULA 3 | | FORMULA 4 | | CONTROL | | DETERGENT | | |
| | HOT | WARM | HOT | WARM | HOT | WARM | HOT | WARM | HOT | WARM | HOT | WARM | LSD |
| INSTRUMENTAL GRADING STAINS: | | | | | | | | | | | | | |
| Chocolate Ice Cream | 99.4 | 99.4 | 99.2 | 99.4 | 99.4 | 99.2 | 99.4 | 99.2 | 98.5 | 99.0 | 98.2 | 98.3 | 0.3 |
| Azocasein | 33.4 | 25.4 | 35.1 | 27.9 | 32.5 | 26.8 | 31.2 | 24.9 | 4.5 | 3.5 | 1.5 | 0. | 3.0 |
| Egg | 99.4 | 99.3 | 99.2 | 99.2 | 99.2 | 98.9 | 99.0 | 98.9 | 99.0 | 98.9 | 98.6 | 97.4 | 1.0 |
| Grass | 96.2 | 95.2 | 95.1 | 94.6 | 92.4 | 94.6 | 95.1 | 91.6 | 75.7 | 77.7 | 63.8 | 72.8 | 2.3 |
| Spaghetti Sauce | 97.9 | 97.0 | 97.5 | 96.8 | 96.7 | 95.8 | 96.6 | 95.4 | 94.2 | 95.0 | 94.2 | 92.4 | 1.1 |
| Dirty Motor Oil | 92.2 | 92.1 | 92.3 | 92.3 | 92.6 | 91.7 | 92.9 | 91.4 | 91.7 | 91.0 | 14.3 | 15.9 | 1.4 |
| Blood | 99.8 | 99.8 | 99.7 | 99.6 | 99.8 | 99.7 | 99.7 | 99.6 | 99.1 | 99.5 | 98.9 | 99.2 | 2.8 |
| VISUAL GRADING STAINS: | | | | | | | | | | | | | |
| Grass | 4.4 | 3.8 | 4.2 | 4.1 | 3.6 | 4.0 | 4.3 | 3.6 | 1.6 | 1.6 | 1.4 | 1.4 | 0.2 |
| Spaghetti Sauce | 4.7 | 4.4 | 4.8 | 4.3 | 4.6 | 4.7 | 4.5 | 4.3 | 4.0 | 4.0 | 3.8 | 3.7 | 0.2 |
| Dirty Motor Oil | 4.1 | 4.3 | 4.4 | 4.2 | 4.4 | 4.5 | 4.5 | 4.3 | 4.1 | 4.1 | 1.0 | 1.0 | 0.2 |
| Blood | 5.0 | 4.9 | 4.9 | 5.0 | 4.9 | 4.9 | 4.9 | 5.0 | 4.7 | 4.9 | 4.9 | 4.9 | 0.1 |
| Ballpoint Ink | 1.8 | 2.2 | 1.8 | 2.4 | 1.7 | 1.9 | 1.9 | 2.0 | 2.0 | 2.7 | 1.1 | 1.1 | 0.2 |

TABLE XII

| | PERFORMANCE EVALUATION 100% POLYESTER | | | | | | | | | | | | |
|---|---|---|---|---|---|---|---|---|---|---|---|---|---|
| | FORMULA 1 | | FORMULA 2 | | FORMULA 3 | | FORMULA 4 | | CONTROL | | DETERGENT | | |
| | HOT | WARM | HOT | WARM | HOT | WARM | HOT | WARM | HOT | WARM | HOT | WARM | LSD |
| INSTRUMENTAL GRADING STAINS: | | | | | | | | | | | | | |
| Chocolate Ice Cream | 99.6 | 99.5 | 99.6 | 99.6 | 99.5 | 99.8 | 99.7 | 99.8 | 99.6 | 99.7 | 99.5 | 99.6 | 0.2 |
| Azocasein | 37.6 | 31.3 | 48.4 | 35.6 | 39.2 | 28.8 | 43.4 | 36.3 | 5.3 | 5.3 | 4.7 | 5.9 | 3.9 |
| Egg | 94.9 | 94.1 | 95.8 | 95.4 | 94.9 | 95.5 | 95.2 | 95.1 | 96.0 | 94.3 | 99.3 | 99.5 | 1.0 |
| Grass | 98.3 | 96.7 | 98.4 | 97.6 | 97.2 | 95.2 | 97.6 | 97.0 | 75.3 | 70.2 | 69.3 | 72.5 | 3.3 |
| Spaghetti Sauce | 98.6 | 95.5 | 97.2 | 96.1 | 95.6 | 95.3 | 97.5 | 96.7 | 96.7 | 97.5 | 96.0 | 92.6 | 1.8 |
| Dirty Motor Oil | 90.8 | 89.3 | 83.7 | 85.3 | 92.0 | 90.9 | 89.0 | 88.5 | 90.5 | 90.5 | 15.3 | 15.5 | 2.0 |

TABLE XII-continued

PERFORMANCE EVALUATION
100% POLYESTER

| | FORMULA 1 | | FORMULA 2 | | FORMULA 3 | | FORMULA 4 | | CONTROL | | DETERGENT | | |
|---|---|---|---|---|---|---|---|---|---|---|---|---|---|
| | HOT | WARM | HOT | WARM | HOT | WARM | HOT | WARM | HOT | WARM | HOT | WARM | LSD |
| Blood | 99.7 | 99.6 | 99.6 | 99.4 | 99.5 | 99.7 | 99.5 | 99.4 | 99.6 | 99.6 | 99.6 | 99.6 | 0.1 |
| VISUAL GRADING STAINS: | | | | | | | | | | | | | |
| Grass | 4.4 | 4.5 | 4.3 | 4.6 | 4.2 | 4.4 | 4.6 | 4.8 | 1.5 | 1.4 | 1.3 | 1.4 | 0.2 |
| Spaghetti Sauce | 4.9 | 4.3 | 4.5 | 4.2 | 4.4 | 4.2 | 4.7 | 4.2 | 4.4 | 4.4 | 4.3 | 3.4 | 0.3 |
| Dirty Motor Oil | 3.5 | 3.4 | 2.8 | 2.8 | 3.8 | 3.5 | 3.1 | 3.4 | 3.7 | 3.7 | 1.0 | 1.2 | 0.2 |
| Blood | — | — | — | — | — | — | — | — | — | — | — | — | — |
| Ballpoint Ink | 2.6 | 3.1 | 3.0 | 2.9 | 2.1 | 1.8 | 2.1 | 2.2 | 2.9 | 3.1 | 1.1 | 1.1 | 0.1 |

The compositions set forth in Table IX above were stored for periods of time up to 2 months at storage temperatures varying between 35° and 100° F. The samples of the compositions were tested against both grass and azocasein stains at intervals up to the 2 months stated above. Table XIII below sets forth the results, thus indicating the enzyme stability in the compositions as a function of time and storage temperature.

TABLE XIII

STABILITY TEST

| | | Formula 1 | | | Formula 2 | | | Formula 3 | | | Formula 4 | | |
|---|---|---|---|---|---|---|---|---|---|---|---|---|---|
| | | Storage temp. | | | | | | | | | | | |
| | Time | 35° | 70° | 100° | 35° | 70° | 100° | 35° | 70° | 100° | 35° | 70° | 100° |
| 1 | 0 | | 95.2% | | | 94.6% | | | 94.7% | | | 91.6% | |
| 2 | 1 mth | 93.3 | 92.8 | 93.8 | 91.3 | 94.4 | 92.2 | 92.2 | 93.2 | 89.3 | 91.7 | 93.2 | 90.8 |
| 3 | 1½ mth | 93.6 | 93.6 | 91.1 | 88.5 | 91.7 | 91.7 | 90.6 | 90.0 | 86.0 | 91.4 | 91.1 | 91.8 |
| 4 | 2 mth | 88.1 | 87.3 | 83.9 | 86.2 | 83.8 | 89.5 | 80.6 | 84.0 | 79.1 | 84.5 | 88.7 | 82.6 |
| 5 | 0 | | 3.8 | | | 4.1 | | | 4.0 | | | 3.6 | |
| 6 | 1 mth | 3.2 | 3.7 | 3.6 | 3.1 | 3.8 | 3.5 | 2.5 | 3.3 | 2.8 | 2.7 | 3.4 | 3.7 |
| 7 | 1½ mth | 3.6 | 4.1 | 3.3 | 3.2 | 3.4 | 3.7 | 2.7 | 2.8 | 2.4 | 3.0 | 3.4 | 3.3 |
| 8 | 2 mth | 2.4 | 2.2 | 1.6 | 2.3 | 1.8 | 2.6 | 1.7 | 2.2 | 1.8 | 2.0 | 1.9 | 1.6 |
| 9 | 0 | | 25.4% | | | 27.9% | | | 26.7% | | | 24.9% | |
| 10 | 1 mth | 20.7 | 21.0 | 19.7 | 16.0 | 21.0 | 22.7 | 24.9 | 18.4 | 12.5 | 21.2 | 14.8 | 16.7 |
| 11 | 1½ mth | 22.1 | 15.5 | 19.0 | 14.5 | 13.0 | 21.2 | 13.1 | 13.1 | 12.4 | 12.1 | 9.7 | 20.5 |
| 12 | 2 mth | 15.0 | 18.8 | 17.2 | 15.0 | 20.3 | 21.4 | 17.2 | 15.1 | 14.9 | 13.4 | 15.3 | 15.2 |

CONTROL: INSTRUMENTAL/GRASS 77.7 ± 2.3%
VISUAL/GRASS 1.6 ± 0.2
INSTRUMENTAL/AZOCASEIN 3.5 ± 3.0%

Note:
1-4 and 9-12 were graded by instrument (% SRox); 5-8 were visually graded (1-5 scale) 1-8 were grass stains; 9-12 were azocasein stains.

Further studies were undertaken to evaluate physical stability in varying compositions prepared according to the invention. Table XIV below sets forth these formulations along with statements concerning their physical stability after storage at various storage temperatures.

TABLE XIV

FORMULAS

| RAW MATERIALS | wt % | wt % | wt % | wt % | wt % | wt % | wt % | wt % | wt % | wt % | wt % | wt % | wt % | wt % |
|---|---|---|---|---|---|---|---|---|---|---|---|---|---|---|
| Savinase 8.0L | 0.1 | 0.1 | 0.1 | 0.1 | 0.1 | 0.1 | 0.1 | 0.1 | 0.1 | 0.1 | 0.1 | 1.0 | 1.0 | 1.0 |
| Petro 22 | 1.0 | 0.0 | 1.0 | 0.0 | 1.0 | 0.0 | 1.0 | 0.0 | 1.0 | 0.0 | 1.0 | 0.0 | 0.0 | 1.0 |
| Ethylene Glycol | 0.0 | 0.0 | 0.0 | 2.5 | 2.5 | 0.0 | 0.0 | 0.0 | 0.0 | 2.5 | 2.5 | 0.0 | 2.5 | 2.5 |
| Neodol 25-3 | 15.2 | 14.7 | 14.6 | 14.3 | 14.2 | 15.3 | 15.2 | 14.7 | 14.6 | 14.3 | 14.2 | 14.6 | 14.2 | 14.1 |
| Biosoft EA-10 | 15.2 | 14.7 | 14.6 | 14.3 | 14.2 | 15.3 | 15.2 | 14.7 | 14.6 | 14.3 | 14.2 | 14.6 | 14.2 | 14.1 |
| Isopar L | 66.9 | 64.9 | 64.1 | 63.2 | 62.4 | 67.7 | 66.9 | 64.9 | 64.1 | 63.2 | 62.4 | 64.6 | 62.9 | 62.1 |
| IM NaCl (aq) | 0.0 | 0.0 | 0.0 | 0.0 | 0.0 | 1.0 | 1.0 | 5.0 | 5.0 | 5.0 | 5.0 | 5.0 | 5.0 | 5.0 |
| Water | 1.0 | 5.0 | 5.0 | 5.0 | 5.0 | 0.0 | 0.0 | 0.0 | 0.0 | 0.0 | 0.0 | 0.0 | 0.0 | 0.0 |
| Perfume | 0.2 | 0.2 | 0.2 | 0.2 | 0.2 | 0.2 | 0.2 | 0.2 | 0.2 | 0.2 | 0.2 | 0.2 | 0.2 | 0.2 |

These formulas were found to be physically stable after 18 days at 35, 70 and 100° F.

| RAW MATERIALS | wt % | wt % | wt % | wt % |
|---|---|---|---|---|
| Savinase 8.0L | 0.2 | 0.2 | 0.2 | 0.2 |
| $CaCl_2$ (0.5M) | 1.5 | 0.0 | 0.0 | 0.0 |
| NaCl (0.5M) | 0.0 | 3.0 | 0.75 | 0.0 |
| Water | 0.0 | 0.0 | 0.0 | 3.0 |
| Propylene Glycol | 2.5 | 0.0 | 0.0 | 0.0 |
| Ethylene Glycol | 0.0 | 2.5 | 2.5 | 2.5 |
| Neodol 25-3 | 14.65 | 13.9 | 15.0 | 13.9 |
| Biosoft EA-10 | 14.65 | 13.9 | 15.0 | 13.9 |
| Isopar L | 66.3 | 66.3 | 66.35 | 66.3 |
| Perfume | 0.2 | 0.2 | 0.2 | 0.2 |

TABLE XIV-continued

| | FORMULAS | | | |
|---|---|---|---|---|
| % Enzyme Activity Remaining After 33 days at 100° F. | 41% | 45% | 43% | 41% |

These formulas were physically stable after 33 days at 35, 70 and 100° F.
Enzyme stability was shown.

TABLE XV below presents some prewash formulations wherein several different enzymes were utilized. These formulations were also tested for performance on various stains.

TABLE XV

| RAW MATERIALS | A (wt %) | B (wt %) | C (wt %) |
|---|---|---|---|
| 1M NaCL | 1.5 | 1.5 | 1.5 |
| Ethylene Glycol | 2.5 | 2.5 | 2.5 |
| Neodol 25-3 | 14.65 | 14.51 | 14.65 |
| Biosoft EA-10 | 14.65 | 14.51 | 14.65 |
| Isopar K | 66.3 | 66.14 | 66.3 |
| Perfume | 0.2 | 0.2 | 0.2 |
| Esperase 8.0L | 0.2 | 0.0 | 0.0 |
| Alcalase 2.5L | 0.0 | 0.64 | 0.0 |
| Savinase 8.0L | 0.0 | 0.0 | 0.2 |

These samples were evaluated for performance on grass, blood and gravy. All three formulas provided a benefit on grass and gravy. The blood stain was totally removed by detergent alone. No enzyme stability test was conducted.

Still another group of compositions were prepared having further variations in formulation. Table XVI below sets forth some compositions wherein additional enzyme stabilizer (triethanolamine-Formula F) was included; or wherein the solvent system (methylester-Formula G) was varied. Table XVI also indicates the residual enzyme activity after storage for the stated period.

Tables XVII, XVIII, and XIX below, present performance data on various fabrics for the compositions of Table XVI.

TABLE XVI

| | FORMULA COMPOSITION | | |
|---|---|---|---|
| | Wt % | | |
| Raw Materials | Formula B | Formula F | Formula G |
| Savinase 8.0L | 0.2 | 0.2 | 0.2 |
| Salt Water (1M NaCl) | 1.5 | 1.5 | 1.5 |
| Neodol 25-3 | 14.65 | 14.65 | 0.0 |
| Biosoft EA-10 | 14.65 | 14.65 | 10.5 |
| Petro 22 | 0.0 | 0.0 | 1.0 |
| Ethylene Glycol | 2.5 | 0.0 | 0.0 |
| Isopar L | 66.3 | 66.3 | 53.6 |
| Perfume | 0.2 | 0.2 | 0.0 |
| Triethanolamine | 0.0 | 2.5 | 0.0 |
| Neodol 91-2.5 | 0.0 | 0.0 | 9.9 |
| Procter and Gamble CE-618 Methylester | 0.0 | 0.0 | 16.9 |
| Diethylene glycol | 0.0 | 0.0 | 6.4 |
| Water (no salt) | 0.0 | 0.0 | 1.0 |
| | 100.0 | 100.0 | 100.0 |
| % Enzyme Activity Remaining after 33 days at 100° F. | 38% | 58% | 43% |

TABLE XVII

PERFORMANCE EVALUATION
100% cotton

| | Formula B | | | Formula F | | | Formula G | | | CONTROL | | | |
|---|---|---|---|---|---|---|---|---|---|---|---|---|---|
| | Wash Temp. | | | | | | | | | | | | |
| | 70° | 100° | 130° | 70° | 100° | 130° | 70° | 100° | 130° | 70° | 100° | 130° | LSD |
| INSTRUMENTAL GRADING | | | | | | | | | | | | | |
| AZOCASEIN | 21.1 | 26.8 | 39.7 | 23.2 | 36.5 | 43.0 | 26.0 | 33.0 | 43.9 | 10.8 | 9.7 | 9.5 | 4.6 |
| BLOOD | 93.8 | 94.5 | 90.1 | 93.3 | 94.7 | 92.7 | 93.8 | 94.7 | 91.3 | 91.0 | 92.2 | 81.1 | 1.8 |
| PERMANENT INK | 53.1 | 56.5 | 57.9 | 44.5 | 45.9 | 52.3 | 54.8 | 58.3 | 59.4 | 54.6 | 56.8 | 59.3 | 3.4 |
| DIRTY MOTOR OIL | 91.2 | 91.5 | 92.6 | 90.3 | 90.0 | 92.5 | 86.9 | 89.3 | 90.4 | 90.8 | 92.4 | 92.8 | 0.8 |
| CHOCOLATE | 76.7 | 79.7 | 80.7 | 76.0 | 77.1 | 78.4 | 75.8 | 79.2 | 81.7 | 76.4 | 77.1 | 78.4 | 1.8 |
| TEA | 24.2 | 31.6 | 42.3 | 16.6 | 23.6 | 27.4 | 29.4 | 32.2 | 42.2 | 22.8 | 34.7 | 42.7 | 2.8 |
| BLUEBERRY | 84.3 | 90.0 | 93.3 | 84.1 | 89.2 | 91.3 | 86.3 | 91.0 | 92.7 | 74.3 | 79.2 | 77.2 | 2.2 |
| BANDY CLAY | 91.9 | 94.6 | 94.3 | 93.6 | 95.0 | 95.3 | 92.7 | 94.8 | 95.6 | 93.4 | 95.8 | 95.5 | 1.3 |
| SEBUM SOIL | 93.0 | 93.8 | 95.3 | 92.7 | 93.8 | 94.2 | 91.9 | 92.5 | 93.6 | 94.4 | 95.1 | 96.0 | 0.7 |
| GRASS | 96.1 | 92.7 | 88.9 | 95.7 | 90.6 | 90.1 | 95.2 | 90.4 | 87.2 | 74.3 | 82.4 | 84.5 | 2.3 |
| VISUAL GRADING | | | | | | | | | | | | | |
| BALLPOINT INK | 2.8 | 2.8 | 3.0 | 2.5 | 2.9 | 2.9 | 2.8 | 3.2 | 3.2 | 3.3 | 3.3 | 3.3 | 0.2 |

TABLE XVIII

PERFORMANCE EVALUATION
65%/35% poly/cotton

| | Formula B | | | Formula F | | | Formula G | | | CONTROL | | | |
|---|---|---|---|---|---|---|---|---|---|---|---|---|---|
| | Wash Temp. | | | | | | | | | | | | |
| | 70° | 100° | 130° | 70° | 100° | 130° | 70° | 100° | 130° | 70° | 100° | 130° | LSD |
| INSTRUMENTAL GRADING | | | | | | | | | | | | | |
| AZOCASEIN | 18.7 | 26.7 | 31.2 | 17.2 | 25.3 | 25.6 | 21.6 | 25.5 | 32.6 | 3.9 | 3.9 | 6.4 | 4.0 |
| BLOOD | 98.5 | 98.3 | 98.5 | 98.4 | 98.5 | 98.5 | 98.6 | 98.4 | 98.6 | 98.1 | 98.5 | 98.4 | 0.2 |
| PERMANENT INK | 55.1 | 58.3 | 64.5 | 47.9 | 50.0 | 51.6 | 58.9 | 63.5 | 67.8 | 56.4 | 59.8 | 62.3 | 1.5 |
| DIRTY MOTOR OIL | 89.8 | 90.3 | 93.9 | 89.6 | 91.9 | 92.8 | 90.3 | 91.2 | 92.4 | 90.3 | 92.0 | 93.3 | 1.6 |
| CHOCOLATE | 90.9 | 91.8 | 89.8 | 88.8 | 89.5 | 88.8 | 92.0 | 91.1 | 90.3 | 89.2 | 89.1 | 90.5 | 1.0 |
| TEA | 41.1 | 43.6 | 51.2 | 30.8 | 30.1 | 34.5 | 45.3 | 45.2 | 50.2 | 38.7 | 44.4 | 48.8 | 3.4 |
| BLUEBERRY | 87.5 | 91.8 | 96.8 | 84.9 | 89.1 | 92.4 | 88.1 | 92.4 | 96.5 | 83.5 | 86.7 | 88.0 | 1.7 |

TABLE XVIII-continued

PERFORMANCE EVALUATION
65%/35% poly/cotton

| | Formula B | | | Formula F | | | Formula G | | | CONTROL | | | |
|---|---|---|---|---|---|---|---|---|---|---|---|---|---|
| | Wash Temp. | | | | | | | | | | | | |
| | 70° | 100° | 130° | 70° | 100° | 130° | 70° | 100° | 130° | 70° | 100° | 130° | LSD |
| BANDY CLAY | 75.6 | 80.0 | 83.2 | 78.3 | 80.6 | 83.1 | 75.8 | 79.4 | 83.0 | 75.1 | 80.2 | 82.0 | 1.7 |
| SEBUM SOIL | 100.4 | 101.9 | 104.0 | 95.3 | 98.7 | 100.8 | 93.6 | 95.6 | 95.9 | 100.7 | 102.4 | 102.3 | 1.9 |
| GRASS | 90.7 | 86.3 | 82.3 | 90.9 | 86.5 | 84.7 | 89.0 | 85.8 | 82.6 | 81.4 | 81.4 | 81.5 | 1.1 |
| VISUAL GRADING | | | | | | | | | | | | | |
| BALLPOINT INK | 2.1 | 2.5 | 2.4 | 2.3 | 2.7 | 2.5 | 2.1 | 2.3 | 2.4 | 2.5 | 2.4 | 2.4 | 0.2 |

TABLE XIX

PERFORMANCE EVALUATION
100% POLYESTER

| | Formula B | | | Formula F | | | Formula G | | | CONTROL | | | |
|---|---|---|---|---|---|---|---|---|---|---|---|---|---|
| | Wash Temp. | | | | | | | | | | | | |
| | 70° | 100° | 130° | 70° | 100° | 130° | 70° | 100° | 130° | 70° | 100° | 130° | LSD |
| INSTRUMENTAL GRADING | | | | | | | | | | | | | |
| AZOCASEIN | 22.6 | 29.8 | 31.4 | 22.2 | 30.6 | 32.9 | — | — | — | 9.8 | 9.9 | 12.0 | 4.0 |
| BLOOD | 96.7 | 96.5 | 96.5 | 96.8 | 96.7 | 96.4 | — | — | — | 97.1 | 96.8 | 97.6 | 0.9 |
| PERMANENT INK | 97.5 | 96.7 | 96.2 | 91.7 | 92.4 | 93.5 | — | — | — | 97.0 | 96.8 | 97.6 | 2.6 |
| DIRTY MOTOR OIL | 91.1 | 90.7 | 90.9 | 92.8 | 92.6 | 90.9 | — | — | — | 93.3 | 92.4 | 91.9 | 1.2 |
| CHOCOLATE | 97.1 | 96.9 | 97.0 | 97.3 | 97.1 | 97.1 | — | — | — | 97.1 | 96.9 | 97.1 | 1.0 |
| TEA | 96.7 | 96.8 | 97.0 | 86.4 | 84.6 | 85.3 | — | — | — | 96.7 | 96.6 | 96.4 | 2.9 |
| BLUEBERRY | 97.8 | 96.9 | 96.6 | 97.3 | 96.6 | 96.6 | — | — | — | 97.9 | 96.6 | 97.0 | 2.1 |
| BANDY CLAY | 98.2 | 94.2 | 99.4 | 98.6 | 98.9 | 99.2 | — | — | — | 98.7 | 99.4 | 99.2 | 0.9 |
| SEBUM SOIL | 94.2 | 95.5 | 95.3 | 96.3 | 96.0 | 95.2 | — | — | — | 95.2 | 95.9 | 95.4 | 1.5 |
| GRASS | 96.4 | 95.3 | 95.8 | 95.9 | 95.2 | 95.2 | — | — | — | 85.7 | 87.7 | 79.8 | 1.7 |
| VISUAL GRADING | | | | | | | | | | | | | |
| BALLPOINT INK | 2.7 | 2.6 | 2.6 | 3.3 | 2.7 | 2.5 | — | — | — | 2.8 | 3.2 | 3.2 | 0.1 |

*NO PERFORMANCE WORK WAS DONE ON POLYESTER WITH FORMULA G DUE TO LACK OF SUFFICIENT SAMPLE.

What is claimed is:

1. A method for improving the storage life of a liquid enzyme composition comprising, by weight, about 60 to 70% hydrocarbon solvent, about 25 to 35% surfactant, about 0.1 to 1.0% enzymes, and less than 5.0% water with a solvent to surfactant ratio of about 2:1, consisting essentially of the steps of sequentially:

(a) mixing the enzymes into an aqueous solution with constant agitation;

(b) then mixing surfactant into the aqueous enzyme solution with constant agitation; and (c) then gradually adding the hydrocarbon solvent to the aqueous enzyme/surfactant mixture with constant agitation whereby the aqueous enzyme/surfactant mixture is encapsulated as reversed micelles in hydrocarbon solvent medium for protecting the enzyme from the hydrocarbon solvent during the steps of the process and producing the resulting soil removal composition product as a clear, stable liquid.

2. The method of claim 1 wherein sodium chloride is added to the aqueous enzyme solution to further stabilize said enzymes.

3. The method of claim 1 wherein said aqueous enzyme solution is combined with the surfactant, and the solvent is then added.

* * * * *